United States Patent [19]
Nobbs et al.

[11] Patent Number: 6,124,308
[45] Date of Patent: Sep. 26, 2000

[54] OPTICALLY ACTIVE PHENYL PYRIMIDINE DERIVATIVES AS ANALGESIC AGENT

[75] Inventors: Malcolm Stuart Nobbs, Stevenage; Sandra Jane Rodgers, Dartford, both of United Kingdom

[73] Assignee: Glaxo Wellcome Inc., Research Triangle Park, N.C.

[21] Appl. No.: 09/029,162

[22] PCT Filed: Sep. 3, 1996

[86] PCT No.: PCT/EP96/03856

§ 371 Date: Feb. 26, 1998

§ 102(e) Date: Feb. 26, 1998

[87] PCT Pub. No.: WO97/09317

PCT Pub. Date: Mar. 13, 1997

[30] Foreign Application Priority Data

Sep. 5, 1995 [GB] United Kingdom .................. 9518027

[51] Int. Cl.⁷ ..................... A61K 31/505; C07D 239/02; C07D 239/22
[52] U.S. Cl. ................ 514/275; 544/322; 544/223; 544/325
[58] Field of Search ................ 544/322, 323, 544/325; 514/275

[56] References Cited

U.S. PATENT DOCUMENTS 5,684,005 11/1997 Miller et al. ..................... 514/275

FOREIGN PATENT DOCUMENTS

| 0 021 121 | 1/1981 | European Pat. Off. . |
| 0372934 | 12/1989 | European Pat. Off. . |
| 0 372 934 | 6/1990 | European Pat. Off. . |
| 0021121 | 1/1991 | European Pat. Off. . |

*Primary Examiner*—John M. Ford
*Assistant Examiner*—Pavanaram K Sripada
*Attorney, Agent, or Firm*—Nixon & Vanderhye

[57] ABSTRACT

A pyrimidine of formula (I)

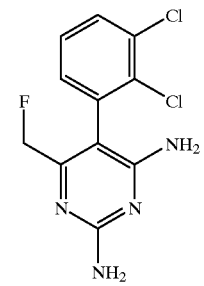

and its pharmaceutically acceptable acid addition salts are useful as analgesics, as anticonvulsants or in the treatment of irritable bowel syndrome or bipolar disorder.

9 Claims, No Drawings

OPTICALLY ACTIVE PHENYL PYRIMIDINE DERIVATIVES AS ANALGESIC AGENT

This application is a 371 of PCT/EP96/03856 filed Sep. 03, 1996.

The present invention relates to a pyrimidine compound, its preparation, pharmaceutical formulations containing it and its use in therapy.

EP-A-21121 discloses a group of 3,5-diamino-6-(substituted phenyl)-1,2,4-triazines which are active in the treatment of central nervous system (CNS) disorders, for example in the treatment of epilepsy. One such triazine is 3,5-diamino-6-(2,3-dichlorophenyl)-1,2,4-triazine which is alternatively called lamotrigine.

EP-0372934-A discloses pyrimidine compounds useful in the treatment of CNS disorders. Example 18 of EP-0372934-A discloses 2,4-diamino-5-(2,3-dichlorophenyl)-6-fluoromethyl pyrimidine.

According to the present invention, there is provided the pyrimidine of formula (I):

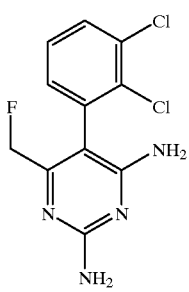

and acid addition salts thereof.

The pyrimidine of formula (I) is R(−)-2,4-diamino-5-(2,3-dichlorophenyl)-6-fluoromethyl pyrimidine. It is substantially free of the corresponding S(+)enantiomer, S(+)-2,4-diamino-5-(2,3-dichlorophenyl)-6-fluoromethyl pyrimidine. The S(+)enantiomer has the formula (II):

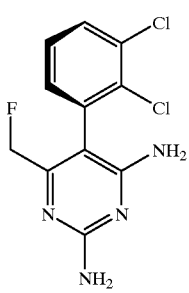

The R(−)enantiomer of the invention has more desirable properties than lamotrigine: it is less active against dihydrofolate reductase (DHFR) and is more active in analgesic and anticonvulsant tests. It also has more desirable properties than the S(+)enantiomer. Thus:

the R(−)enantiomer has a better pharmacokinetic profile than the S(+) enantiomer, for example it is less rapidly metabolised and therefore has a longer half-life (duration of action);

the R(−)enantiomer exhibits superior analgesic activity to the S(+)enantiomer;

the R(−)enantiomer exhibits superior anticonvulsant activity to the S(+)enantiomer; and the R(−)enantiomer exhibits less activity against DHFR than the S(+)enantiomer.

It is surprising that the R(−)enantiomer is better then the S(+)enantiomer in all of these respects. The R(−)enantiomer can be provided substantially pure. Thus, the ratio R(−) enantiomer: S(+)enantiomer may be at least 94:6 such as at least 98:2 or at least 99:1. Preferably the R(−)enantiomer is provided having an isomeric purity of at least 99.5%.

The R(−)enantiomer and acid addition salts thereof can be prepared according to the invention by a first process which comprises:

(i) resolving racemic 2,4-diamino-5-(2,3-dichlorophenyl)-6-fluoromethyl pyrimidine with a suitable chiral acid and recrystallising the resulting salt so as to obtain a salt which consists substantially only of the salt with R(−)-2,4-diamino-5-(2,3-dichlorophenyl)-6-fluoromethyl pyrimidine; and (ii) if desired, converting the recrystallised salt to the free base or another acid addition salt as appropriate.

The resolution step (i) is achieved with a suitable chiral acid in a suitable solvent. Preferably the acid is (−)-dibenzoyl-L-tartaric acid. Other suitable acids may be determined by testing. Preferably the solvent is ethanol. Again, though, other suitable solvents may be determined by testing.

The resulting salt, which may be isolated, consists predominantly of the salt with R(−)-2,4-diamino-5-(2,3-dichlorophenyl)-6-fluoromethyl pyrimidine. A minor proportion of the salt with the S(+)enantiomer may be present. The proportion of the salt with the R(−)enantiomer can be increased by effecting one or more, for example two or three, recrystallisations in step (i).

To this end, the crystalline salt obtained as a result of resolution may be dissolved in a solvent therefor. This may be achieved by warming. The salt is recrystallised from the resulting solution. That may be achieved by allowing the solution to cool. The solvent may be ethanol. The proportion of the salt with the R(−)enantiomer can thus be increased until it is substantially pure, i.e. until substantially only the salt with the R(−) enantiomer is present.

The mother liquor from the resolution step and the mother liquor from the or each recrystallisation step are enriched with the S(+)enantiomer. One or more of these liquors or the pooled liquors may be treated with a base such as sodium hydroxide to remove any residual chiral acid and to afford thereby the free base. The free base obtained may be dried.

The free base enriched in the S(+) enantiomer cain then be converted to the racemate. That may be achieved by heating under reflux in a solvent, such as toluene, for example for from 12 to 48 hours. The racemate thus obtained can then be recycled to step (i) of the present process. Yields can thus be increased.

The salt that is obtained in step (i) is the salt of the chiral acid used for resolution and of the R(−)enantiomer, substantially, free of the S(+)enantiomer. This salt can be converted to the free base or another acid addition salt according to step (ii) of the present process. The salt of the chiral acid and the R(−)enantiomer may thus be treated in solution with a base such as sodium hydroxide to obtain the free base. The free base can itself then be converted into an acid addition salt thereof.

Suitable acid addition salts which may be formed in step (ii) include those formed with either organic or inorganic acids. Such acid addition salts will normally be pharmaceutically acceptable. Thus, suitable salts include those formed with hydrochloric, hydrobromic, sulphuric, citric, tartaric, phosphoric, lactic, pyruvic, acetic, succinic, fumaric, maleic, oxaloacetic, methanesulphonic, ethanesulphonic, p-toluenesulphonic, benzenesulphonic and isethionic acids. These salts can be made by reacting the free base with the appropriate acid. Preferred salts are the hydrochloride, sulphate, phosphate, methanesulphonate and isethionate salts. The hydrochloride and methanesulphonate salts are particularly suitable for intravenous administration.

The R(−)enantiomer and acid addition salts thereof can alternatively be prepared according to the invention by a second process which comprises:

(a) resolving racemic 2,4-diamino-5-(2,3-dichlorophenyl)-6-hydroxymethyl pyrimidine with a suitable chiral acid and recrystallising the resulting salt so as to obtain a salt which consists substantially only of the salt with (−)-2,4-diamino-5-(2,3-dichlorophenyl)-6-hydroxymethyl pyrimidine;

(b) if desired, converting the recrystallised salt to the free base or another salt;

(c) fluorinating the recrystallised salt from step (a) or the free base or said other salt from step (b) under conditions at which racemisation of the (−)-2,4-diamino-5-(2,3-dichlorophenyl)-6-hydroxymethyl pyrimidine or the resulting R(−)-2,4-diamino-5-(2,3-dichlorophenyl)-6-fluoromethyl pyrimidine does not occur; and (d) if desired, converting the resulting fluorinated compound into the free base or into an acid addition salt thereof as appropriate.

The resolution step (a) is achieved with a suitable chiral acid in a suitable solvent. Preferably the acid is (+)-di-p-toluoyl-D-tartaric acid. Other suitable acids may be determined by testing. Preferably the solvent is ethanol. Again, though, other suitable solvents may be determined by testing.

The resulting salt, which may be isolated, consists predominantly of the salt with (−)-2,4-diamino-5-(2,3-dichlorophenyl)-6-hydroxymethyl pyrimidine. A minor proportion of the salt with the (+)enantiomer may be present. The proportion of the salt with the (−)enantiomer can be increased by, effecting one or more, for example two or three, recrystallisations in step (a) of the process.

The crystalline salt obtained as a result of resolution may therefore be dissolved in a solvent therefor. This may be achieved by warming. The salt is recrystallised from the resulting solution. That may be achieved by allowing the solution to cool. The solvent may be ethanol. The proportion of the salt with the (−)enantiomer can thus be increased until it is substantially pure, i.e. until substantially only the salt with the (−)enantiomer is present.

The mother liquor from the resolution step and the mother liquor from the or each recrystallisation step are enriched with the (+)enantiomer. One or more of these liquors or the pooled liquors may be treated with a base such as sodium hydroxide to remove any residual chiral acid and to afford thereby the free base. The free base obtained may be dried.

The free base enriched in the S(+) enantiomer can then be converted to the racemate. That may be achieved by heating under reflux in a solvent, such as toluene, for example for from 12 to 48 hours. The racemate thus obtained can then be recycled to step (a) of the present process. Yields of the (−)enantiomer can thus be increased.

The salt that is obtained as a result of these procedures is the salt of the chiral acid used for resolution and the (−)enantiomer of 2,4-diamino-5-(2,3-dichlorophenyl)-6-hydroxymethyl pyrimidine. The (−)enantiomer has the formula (III):

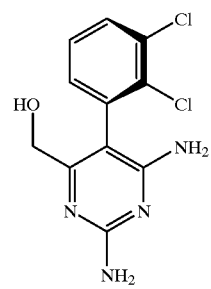

(III)

The (+)enantiomer has the formula (IV):

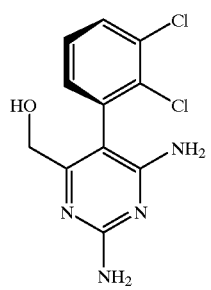

(IV)

The salt of the chiral acid and the (−)enantiomer, substantially free of the (+)enantiomer, can be converted to the free base or another salt according to step (b) of the present process. The chiral acid salt may thus be treated in solution with a base such as sodium hydroxide to obtain the free base.

Fluorination of (−)-2,4-diamino-5-(2,3-dichlorophenyl)-6-hydroxymethyl pyrimidine is effected in step (c). The (−)enantiomer may be present either in the form of a salt or as the free base. Whichever is the case, the (−) enantiomer is substantially free of the (+)enantiomer. Substantially only R(−)-2,4-diamino-5-(2,3-dichlorophenyl)-6-fluoromethyl pyrimidine results, therefore.

The fluorination is effected under conditions at which racemisation of the 6-hydroxymethyl and 6-fluoromethyl (−)enantiomers does not occur. The temperature should thus be less than 80° C., for example less than 50° C. Fluorination can be effected, for example, by the reaction of (−)-2,4-diamino-5-(2,3-dichlorophenyl)-6-hydroxymethyl pyrimidine with diethylaminosulphur trifluoride (DAST). That may be achieved in dichloromethane at −78° C. The solution is then stirred whilst allowing to warm to −10° C. over four and a half hours to give (−)2,4-diamino-5-(2,3-dichlorophenyl)-6-fluoromethyl pyrimidine.

As appropriate, the resulting fluorinated compound may be converted to the free base or into an acid addition salt thereof. Suitable acid addition salts have been noted above. These salts may be made by treating the R(−)enantiomer in free base form with the appropriate acid. The first process according to the invention starts from racemic 2,4-diamino-5-(2,3-dichlorophenyl)-6-fluoromethyl pyrimidine. That can be prepared in two ways:

Process 1

2,3-Dichlorobenzaldehyde is cleanly reduced using sodium borohydride, for example in a toluene/methanol mixture. On decomposition of the excess borohydride, the resulting suspension of 2,3-dichlorobenzyl alcohol is treated with methanesulphonyl chloride to afford the methanesulphonate which is directly converted with aqueous potassium cyanide in the presence of a phase transfer catalyst to 2,3-dichlorophenyl acetonitrile.

A Claisen type condensation between 2,3-dichlorophenyl acetonitrile and ethyl fluoroacetate in the presence of sodium methoxide in methanol affords the sodium enolate. Adjustment of the pH affords crude 2-(2,3-dichlorophenyl)-4-fluoro-3-hydroxy-2-butenenitrile.

Alkylation of 2-(2,3-dichlorophenyl)-4-fluoro-3-hydroxy-2-butenenitrile can suitably be achieved using ethyl iodide in dimethylformamide in the presence of potassium carbonate to afford crude 2-(2,3-dichlorophenyl)-3-ethoxy-4-fluoro-2-butenenitrile.

Coupling of 2-(2,3-dichlorophenyl)-3-ethoxy-4-fluoro-2-butenenitrile with guanidine hydrochloride in the presence of sodium methoxide in methanol affords racemic 2,4-diamino-5-(2,3-dichlorophenyl)-6-fluoromethyl pyrimidine.

Process 2

2,3-Dichlorobenzaldehyde is cleanly reduced using an alkaline solution of sodium borohydride in methanol to afford 2,3-dichlorobenzyl alcohol.

Treatment of 2,3-dichlorobenzyl alcohol with methanesulphonyl chloride in toluene affords the methanesulphonate which is directly converted with aqueous potassium cyanide in the presence of a phase transfer catalyst to 2,3-dichlorophenyl acetonitrile.

A Claisen type condensation between 2,3-dichlorophenyl acetonitrile and ethyl diethoxyacetate in dimethoxyethane in the presence of potassium t-butoxide affords the potassium enolate. Alkylation of the potassium enolate is achieved using ethyl iodide to yield crude 2-(2,3-dichlorophenyl)-3,4,4-triethoxy-but-2-ene nitrile.

Coupling of 2-(2,3-dichlorophenyl)-3,4,4-triethoxy-but-2-ene nitrile with guanidine hydrochloride in the presence of sodium ethoxide in ethanol affords 2,4-diamino-5-(2,3-dichlorophenyl)-6-diethoxymethyl pyrimidine.

Hydrolysis of 2,4-diamino-5-(2,3-dichlorophenyl)-6-diethoxymethyl pyrimidine in aqueous hydrochloric acid at 90° C. affords, on cooling and neutralisation, 2,4-diamino-5-(2,3-dichlorophenyl)-6-formyl pyrimidine.

Sodium borohydride reduction of 2,4-diamino-5-(2,3-dichlorophenyl)-6-formyl pyrimidine in ethanol affords racemic 2,4-diamino-5-(2,3-dichlorophenyl)-6-hydroxymethyl pyrimidine.

Fluorination of racemic 2,4-diamino-5-(2,3-dichlorophenyl)-6-hydroxymethyl pyrimidine can be effected using diethylaminosulphur trifluoride (DAST). That may be carried out in dichloromethane at, initially, −78° C. followed by warming to −10° C. for four and a half hours, to afford racemic 2,4-diamino-5-(2,3-dichlorophenyl)-6-fluoromethyl pyrimidine.

The second process according to the invention starts from racemic 2,4-diamino-5-(2,3-dichlorophenyl)-6-hydroxymethyl pyrimidine. That can be prepared as described in Process 2.

The compound of formula (I) and pharmaceutically acceptable acid addition salts thereof are useful as analgesics. They are therefore useful in treating or preventing pain. They may be used to improve the, condition of a host, typically a human being, suffering from pain. They may be employed to alleviate pain in a host. Thus, the compound of formula (I) and its pharmaceutically acceptable acid addition salts may be used as a preemptive analgesic for postoperative pain; to treat acute pain, for example postoperative pain such as pain following a dental extraction; and to treat chronic pain such acs chronic inflammatory pain, neuropathic pain and cancer pain. Neuropathic pain as described herein may include, for example, AIDS neuropathy, post herpetic neuralgia, diabetic neuropathy and trigeminal neuralgia. The compound of formula (I) may also be used in the treatment or prevention of pain associated with migraine.

The compound of formula (I) and pharmaceutically acceptable acid addition salts thereof are further useful in the treatment of functional bowel disorders, which include non-ulcer dyspepsia, non-cardiac chest pain and in particular irritable bowel syndrome. Irritable bowel syndrome is a gastrointestinal disorder characterised by the presence of abdominal pain and altered bowel habits without any evidence of organic disease. The compound of formula (I) or salt thereof may thus be used to alleviate pain associated with irritable bowel syndrome. The condition of a human patient suffering from irritable bowel syndrome may thus be improved.

The compound of formula (I) and pharmaceutically acceptable acid addition salts thereof are also useful as anticonvulsants. They are therefore useful in treating epilepsy. They may be used to improve the condition of a host, typically a human being, suffering from epilepsy. They may be employed to alleviate the symptoms of epilepsy in a host.

The compound of formula (I) and pharmaceutically acceptable acid addition salts thereof are additionally useful in the treatment of bipolar disorder, alternatively known as manic depression. Type I or II bipolar disorder may be treated. The compound of formula (I) or salt thereof may thus be used to improve the condition of a human patient sufferings from bipolar disorder. They may be used to alleviate the symptoms of bipolar disorder in a host. The compound of formula (I) may also be used in the treatment of unipolar depression.

Still further, the compound of formula (I) and pharmaceutically acceptable acid addition salts thereof are also useful in preventing or reducing dependence on, or preventing or reducing tolerance or reverse tolerance to, a dependence—inducing agent. Examples of dependence inducing agents include opioids (eg morphine), CNS depressants (eg ethanol), psychostimulants (eg cocaine) and nicotine.

The compound of formula (I) and pharmaceutically acceptable acid addition salts thereof may also be useful in the treatment of neurodegenerative diseases, such as Alzheimer's disease, ALS, motor neuron disease and in particular, Parkinson's disease. The compound of formula (I) may also be used in the treatment of neurodegeneration following stroke, traumatic brain injury or the like.

There is therefore further provided by the present invention, use of a compound of formula (I) in the manufacture of a medicament for use in the treatment of a disorder substantially as hereinbefore described. The present invention further comprises a method of treating a patient suffering from, or susceptible to, a disorder substantially as hereinbefore described, which method comprises administering to the patient a therapeutically effective amount of a compound of formula (I).

The precise amount of the compound of formula (I) or salt thereof administered to a host, particularly a human patient, will be the responsibility of the attendant physician. However, the dose employed will depend upon a number of factors including the age and sex of the patient, the precise condition being treated and its severity, and the route of administration.

The compound of formula (I) and its salts may be administered at a dose of from 0.1 to 30 mg/kg body weight per day, calculated as the free base. The dose range for adult human beings is generally from 8 to 2400 mg/day, preferably from 35 to 1050 mg/day, calculated as the free base.

While it is possible for the compound of formula (I) or a pharmaceutically acceptable acid addition salt thereof to be administered as the raw chemical, it is preferable to present it as a pharmaceutical formulation. The formulations of the present invention comprise the compound of formula (I) or a pharmaceutically acceptable acid addition salt thereof together with one or more acceptable carriers or diluents therefor and optionally other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intrathecal, intramuscular and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compound of formula (I) or a pharmaceutically acceptable acid addition salt thereof ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding), optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The Formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

In addition to the ingredients particularly mentioned above, the formulations may include other agents conventional in the art having regard to the type of formulation in question, for example those suitable for oral administration may include flavouring agents.

Preferred unit dosage formulations are those containing an effective daily dose, as hereinabove recited, or an appropriate fraction thereof, of the active ingredient. Conveniently that may be from 5 mg to 500 mg, more conveniently from 10 mg to 250 mg and most conveniently 20 mg to 200 mg, calculated as the free base.

The following Examples illustrate the invention. Reference Examples are provided.

REFERENCE EXAMPLE 1

Synthesis of Racemic (+/−)-2,4-Diamino-5-(2,3-dichlorophenyl)-6-fluoromethylpyrimidine 1. Preparation of 2,3-Dichlorophenylacetonitrile To a suspension of 2,3-dichlorobenzaldehyde (40 kg, 228.6 mole) in toluene (254 liters) and methanol (40 liters), was added sodium borohydride (2.59 kg, 68.6 mole) portionwise over a period of 1 hour. The mixture was stirred for a period of 30 minutes prior to treatment with acetone (20 liters). On decomposition of the excess borohydride, water (80 liters) was added. Toluene (54 liters) was added to the toluene phase and the suspension was warmed to 42° C.±2° C. to attain a solution prior to separation. The organic phase was distilled to remove 54 liters of azeotrope and so effect the removal of water, acetone, and isopropyl alcohol.

The resulting toluene solution of 2,3-dichlorobenzyl alcohol was cooled. To the resulting suspension was added triethylamine (27.8 kg, 274.3 mole) followed by methanesulphonyl chloride (31.4 kg, 274.3 mole) over a period of 1½ hours so as to maintain the temperature at 0° C.±2° C.

The mixture was stirred for 1 hour then water (,100 liters) was charged to the suspension and the mixture was stirred vigorously prior to separation.

To the methanesulphonate in the toluene phase was added tetrabutylammonium hydrogen sulphate (15.6 kg, 45.8 mole) and aqueous potassium cyanide solution (22.4 kg, 342.8 mole) in water (70 liters) over a period of 40 minutes.

The two phase mixture was stirred overnight, separated and the organic phase was washed with water (70 liters). The toluene phase was distilled to remove 130 kg of toluene in the presence of charcoal (2.8 kg) and dicalite (2.8 kg). Petroleum ether 60/80 (300 liters) was charged to the residue, the mixture was filtered hot and crystallised under vacuum to afford 2,3-dichlorophenylacetonitrile (30 kg, 72% yield).

2. Preparation of 2-(2,3-Dichlorophenyl)-3-ethoxy-4-fluoro-2-butenenitrile

To a suspension of 2,3-dichlorophenylacetonitrile (45 kg, 241.9 mole) in methanol (90 liters) was charged 30% w/w sodium methoxide in methanol solution (113.5 kg, 630.6 mole) then ethylfluoroacetate (29.7 kg, 280.1 mole). The reaction mixture was stirred overnight and the product was precipitated from aqueous hydrochloric acid (6:3.7 kg, 648 mole) in water (350 liters). The slurry was filtered and the solid was dissolved in ethyl acetate and washed with brine solution. Ethyl acetate (100 liters) was removed by vacuum distillation. DMF (70 liters) was added and the distillation continued to remove the remaining ethyl acetate.

To the resulting enol in DMF was added potassium carbonate (20 kg, 145 mole) over a period of 10 minutes.

Alkylation of the potassium enolate was achieved using ethyl iodide (37.7 kg, 241.9 mole) at 70° C. for 1¼ hours. The reaction mixture was partitioned between toluene (140 liters) and water (75 liters) and the toluene phase was washed with water (50 liters). Toluene (75 liters) was removed by distillation to afford the crude product as a toluene solution.

3. Preparation of racemic (+/−) 2,4-Diamino-5-(2,3-dichlorophenyl)-6-fluoro methylpyrimidine To guanidine hydrochloride (25.4 kg, 266 mole) in methanol (60 liters) was added 30% w/w sodium methoxide in methanol solution (49.2 kg, 273.3 mole). The suspension was heated to 55° C.±2° C. The toluene solution of 2-(2,3-dichlorophenyl)-3-ethoxy-4-fluoro-2-butenenitrile was added over a period of 45 minutes and the resultant mixture was boiled under reflux for 4 hours, cooled then quenched into water (230 liters). The solid precipitate was washed with 5 portions of methanol (25 liters) to yield the racemate as an off white solid (26.3 kg, 38% yield from 2,3-dichlorophenylacetonitrile).

REFERENCE EXAMPLE 2

Alternative Synthesis of Racemic (+/−) 2,4-Diamino-5-(2,3-dichlorophenyl)-6-fluoromethylpyrimidine 1. Preparation of 2,3-Dichlorobenzyl alcohol To 2,3-dichlorobenzaldehyde (500 g, 2.85 mole) in methanol (3.5 liters) was added an alkaline solution of sodium borohydride (113.5 g, 2.975 mole) in 0.2N sodium hydroxide solution (241 ml) over a period of 1 hour. After 2 hours the reaction mixture was quenched into water (3.7 liters) and the pH was adjusted to pH 6 using glacial acetic acid (125 ml). Filtration afforded 2,3-dichlorobenzyl alcohol as a white solid (467 g, 92% yield).

2. Preparation of 2,3-Dichlorophenylacetonitrile

To the 2,3-dichlorobenzyl alcohol (470.5 g, 2.658 mole) in toluene (1.97 liters) was added triethylamine (322.8E g, 3.19 mole) and dimethylaminopyridine (16.23 g, 0.13 mole). Methanesulphonyl chloride (365.4 g, 3.19 mole) was added over a period of 1 hour. After 2 hours the toluene solution was washed with water.

To the methanesulphonate in toluene was added a solution of tetrabutylammonium hydrogen sulphate (180.5 g, 0.53 mole) in water (641 ml) followed by aqueous potassium cyanide solution (259.6 g 3.987 mole) in water (712 ml). The two phase reaction mixture was stirred overnight, separated and the organic phase was washed with water (1069 ml). The toluene was removed under vacuum and the product was precipitated from petroleum ether 60/80 (1069 ml), filtered and washed with petroleum ether 60/80 (356 ml) to give the crude 2,3-dichlorophenylacetonitrile (406 g, 83% yield).

3. Preparation of 2-(2,3-Dichlorophenyl )-3,4,4-triethoxy-but-2-enenitrile

To 2,3-dichlorophenylacetonitrile (100 g, 0.5,1 mole) in dimethoxyethane (750 ml) and ethyl diethoxyacetate (142 g, 0.81 mole) was added potassium-t-butoxide in 1 portion. The mixture was boiled under reflux for 4½ hours, cooled prior to the addition of ethyl iodide (169.8 g, 1.08 mole) and then heated at 65° C. overnight. The mixture was cooled and concentrated to a residue which was partitioned between water (1.5 liters) and ethyl acetate (1 liter). The aqueous was extracted with ethyl acetate (1 liter) and the combined organic phase was washed with water (500 ml), dried over $MgSO_4$ and evaporated in vacuo to give the desired enol ether as an oil which was used without further purification.

4. Preparation of 2,4-Diamino-5-(2,3-dichlorophenyl)-6-diethoxy methylpyrimidine To guanidine hydrochloride (308.1 g, 3.24 mole) was added sodium ethoxide in ethanol (1.15 kg, 3.54 mole) and ethanol (3 liters). To the resultant mixture was added the crude enol ether (664 g, 1.62 mole) and a further portion of ethanol (1.85 liters). After ai period of 2 hours at room temperature, the mixture was heated to 65° C. overnight, concentrated to a residue and then quenched into water (5 liters). The precipitate was filtered, washed with water (1 liter) and partitioned between warm ethyl acetate (9 liters) and water (1 liter). The organic phase was cooled and filtered to yield the diethoxymethylpyrimidine (207 g). The mother liquor was concentrated to a residue which was recrystallised from isopropyl alcohol (2.5 liters) to yield a further 159 g, total yield (266 g, 63%).

5. Preparation of 2,4-Diamino-5-(2,3-dichlorophenyl)-6-formylpyrimidine

To aqueous hydrochloric acid (232 ml) in water (6.5 liters) was added the diethoxymethylpyrimidine (315 g, 0.88 mole). The mixture was heated to 90° C. for 2 hours and cooled prior to neutralisation to afford 2,4-diamino-5-(2,3-dichlorophenyl)-6-formylpyrimidine as an oligomeric derivative (218 g, 87% yield).

6. Preparation of (+/−)-2,4-Diamino-5-(2,3-dichlorophenyl)-6-hydroxymethylpyrimidine Method A To a suspension of the formylpyrimidine (64 g, 0.23 mole) in ethanol (343 ml) was added sodium borohydride (3.4 g, 0.09 mole). Ethyl acetate (262 ml) was added on completion of the reaction as determined by TLC and the mixture was stirred overnight, filtered and washed with ethanol.

The solid was slurried in water (2 liters), filtered, washed with water (1 liter) and dried to give a cream solid (43.8 g, 68%). Second crops were obtained by concentrating the ethanol filtrate to a residue and slurrying in ethyl acetate (5 volumes) to give the required product (4.3 g, 6.6%). Total yield (48.14 g, 75%).

Method B

To a slurry of the formylpyrimidine (52.3 g, 0.18 mole) in ethanol (250 ml) was added sodium borohydride (5 g, 0.13 mole). The resultant suspension was stirred at room temperature until the reaction was complete, as determined by a suitable analytical technique (TLC), prior to the addition of water (750 ml). The slurry was filtered and washed with water (3×250 ml) and dried to give the required product (40.8 g, 78% yield).

7. Preparation of Racemic (+/−)-2,4-Diamino-5-(2,3-dichlorophenyl)-6-fluoromethylpyrimidine The racemic hydroxymethylpyrimidine (125 g, 438.6 mmol) was cooled in dichloromethane (1.25 liters) to −78° C. Diethylaminosulphur trifluoride (DAST) (291.67 g, 2193 mmol) was added in one portion. The resultant mixture was stirred at −78° C. for 1 hour prior to warming to −10° C. at which temperature it was stirred for 4½ hours. Saturated sodium bicarbonate solution (3.5 liters) was added over a period of 90 minutes to pH 7.

The aqueous and organic phases were decanted from the organic precipitate, separated and the aqueous phase was extracted with ethyl acetate (2×1½ liters). The organic phases were combined and washed with brine solution, dried over $Na_2SO_4$ and $MgSO_4$, filtered and concentrated to yield a yellow solid which was combined with the orange precipitate and triturated with methanol to give the required product as a white solid. Further crops were obtained on concentration of the methanol liquors (110 g, 87%).

REFERENCE EXAMPLE 3

Resolution Using Chiral Acids

1. General Method $10^{-4}$ Mole of a chiral acid was mixed with $10^{-4}$ mole of racemic 2,4-diamino-5-(2,3-dichlorophenyl)-6-fluoromethyl pyrimidine or racemic 2,4-diamino-5-(2,3-dichlorophenyl)-6-hydroxymethyl pyrimidine. To the mixture was added 1 ml of absolute ethanol. The mixture was warmed to allow the solids to dissolve and then allowed to crystallise. Decanting and washing afforded the resulting salts which were then analysed by chiral HPLC or NMR using a chiral shift reagent (R-2,2,2-trifluoro-9-anthryl ethanol). The following chiral acids were tested:

1. (+)-Dibenzoyl-D-tartaric acid monohydrate.
2. (+)-Di-p-toluoyl-D-tartaric acid.
3. (−)-Dibenzoyl-L-tartaric acid monohydrate.
4. (−)-Di-p-toluoyl-L-tartaric acid.
5. (S)(+)O'-Acetyl mandelic acid.
6. 1 R(−)camphor-10-sulphonic acid.
7. R(−)mandelic acid.
8. S(+)mandelic acid.
9. 1R,3R,4R,5R(−)quinic acid.
10. L(−)malic acid.
11. L(+)Tartaric acid.
12. (+)Tartaric acid (dextro).
13. 1R,3S(+)camphoric acid.
14. L(−)Tartaric acid.
15. (1S)(+)3-Bromocamphor-10-sulphonic acid monohydrate.
16. S(+)1,1-Binaphthyl 2,2'-diyl hydrogen phosphate.
17. R(−)1,1-Binaphthyl 2,2'-diyl hydrogen phosphate.
18. D(+)malic acid.
19. (1S)(+)camphor-10-sulphonic acid.
20. 2,3:4,6-Di-O,O-isopropylidene-2-keto-L-glyonic acid monohydrate.

2. 2,4-Diamino-5-(2,3-dichlorophenyl)-6-fluoromethyl Pyrimidine

Fifteen salts from the twenty acids used were crystallised. Only (−)-dibenzoyl-L-tartaric acid and (+)-dibenzoyl-D-tartaric acid afforded resolution, with the former giving an enhanced ratio of the R(−)enantiomer to the S(+)enantiomer.

3. 2,4-Diamino-5-(2,3-dichlorophenyl)-6-hydroxymethyl pyrimidine

Eleven salts from the twenty acids used were crystallised. Of these, (+)-di-p-toluoyl-D-tartaric acid afforded an enhanced ratio of the R(−)enantiomer to the S(+)enantiomer.

4. Solvents

Solvents such as butanone, acetone, methanol and ethylacetate can also be used to effect resolution.

In addition, solvents such as isopropyl alcohol, n-butanol and mixtures of water with either methanol, acetone or ethanol can be used to effect the resolution of (+/−) 2,4-diamino-5-(2,3-dichlorophenyl)-6-fluoromethyl pyrimidine.

EXAMPLE 1

Preparation of R(−)-2,4-diamino-5-(2,3-dichlorophenyl)-6-fluoromethyl Pyrimidine by Small Scale Resolution 1. To racemic (+/−)2,4-diamino-5-(2,3-dichlorophenyl)-6-fluoromethyl pyrimidine (0.8006 g) in a flask was added (−)-dibenzoyl-L-tartaric acid.H$_2$O (1.0490 g). Absolute ethanol (27.7 ml) was added, the mixture was warmed and the resulting solution was left overnight. The mother liquor was then decanted from the white crystalline solid that had formed. The solid was dried in a vacuum oven at 50° C. overnight. The yield of crystalline material obtained (0.9534 g) was about 52%.

The ratio of R(−)-2,4-diamino-5-(2,3-dichlorophenyl)-6-fluoromethyl pyrimidine ("R(−)enantiomer") to S(+)-2,4-diamino-5-(2,3-dichlorophenyl)-6-fluoromethyl pyrimidine ("S(+)enantiomer") was 81:19.

2. Crystalline material (0.8796 g) obtained in the initial resolution step 1 was dissolved under warming in absolute ethanol (36 ml). The solution was left to cool overnight. The mother liquor was decanted. The white crystalline solid obtained was dried in a vacuum oven at 50° C. overnight; yield (0.6111 g) 69%. The ratio of R(−)enantiomer to S(+)enantiomer was 94:6%.

3. Recrystallised material (0.5227 g) from step 2 was dissolved under warming in absolute ethanol (25 ml). The resulting solution was left to cool overnight. The mother liquor was then decanted. The remaining white crystalline solid was washed with ethanol (1 ml) and dried at 50° C. in a vacuum oven overnight; yield (0.397 g) 76%. The ratio of R(−) enantiomer to S(+)enantiomer was 99.8:0.2.

4. The crystalline salt from step 3 was then basified with 2M NaOH solution. Thus, distilled water was added to the salt. The resulting slurry was stirred at room temperature. Then 2M NaOH was added until pH 12 was maintained. The resulting suspension was left for 1 hour. Then the solid was filtered off and washed with water. The wet solid was dried at 50° C. in vacuo to give a white solid.

EXAMPLE 2

Preparation of R(−)-2,4-diamino-5-(2,3-dichlorophenyl)-6-fluoromethyl Pyrimidine by Large Scale Resolution 1. To racemic (+/−)2,4-diamino-5-(2,3-dichlorophenyl)-6-fluoromethyl pyrimidine (78.83 g) in a flask, (−)-dibenzoyl-L-tartaric acid.H$_2$O (103.27 g) was added followed by absolute ethanol (2727 ml). The mixture was heated to reflux until all solids were in solution. The solution was left over 18 hours to cool to room temperature. The white solid formed was filtered off and dried in vacuo for 3 hours at 50° C. The dried solid was recrystallised from absolute ethanol twice (2×1500 ml). The white crystalline solid obtained was dried at 50° C. in vacuo for 6 hours. The ratio of R(−)enantiomer to S(+)enantiomer in the dried crystalline material obtained (22 g) was >99:1.

2. The mother liquors from the recrystallisations were concentrated in vacuo and then treated with 2M NaOH (aqueous solution) to basify the salt. Thus, water (100 ml) was added to the salt (98 g) followed by 2M NaOH solution (250 ml) in 50 ml portions while the suspension was vigorously stirred. The suspension was maintained at pH 12 for 2 hours. The white solid was filtered off and washed with water (5×50 ml) until pH7 was maintained. The solid was dried in vacuo at 50° C. for 4 hours to afford the free base (39 g). The ratio of R(−)enantiomer to S(+)enantiomer in the dried free base was 30:70.

3. The free base enriched with the S(+) enantiomer was then recycled to the racemate. Thus, toluene (500 ml) was added to the free base (399). The mixture was heated at reflux for 24 hours and then cooled to room temperature. A brown solid was filtered off which was dried in vacuo at 50° C. for 3 hours. The ratio R(−)enantiomer: S(+)enantiomer in the dried material obtained (33 g) was 50:50.

4. This racemate was then submitted to step 1 to obtain more of the R (−)enantiomer of >99% enantiomeric purity. The combined salts were then basified with 2M NaOH solution. Thus, distilled water (250 ml) was added to the salts (86.6 g) and the slurry stirred at roam temperature. Then 2M NaOH (154 ml) was added in 50 ml portions and then two 2 ml portions until pH 12 was maintained. The resulting suspension was left for 1 hour and then the solid was filtered off and washed with water (7×100 ml). The wet solid was dried at 50° C. in vacuo to give, for this batch, a buff-coloured solid (37.9 g). Other batches however gave a whites solid. The ratio of the R(−)enantiomer to the S(+) enantiomer in the dried material was 99.7:0.3. Chemical purity=99.2%

EXAMPLE 3

Preparation of R(−)-2,4-diamino-5-(2,3-dichlorophenyl)-6-fluoromethyl Pyrimidine from (−)-2,4-diamino-5-(2,3-dichlorophenyl)-6-hydroxymethyl Pyrimidine 1. Preparation of (−)-2,4-diamino-5-(2,3-dichlorophenyl)-6-hydroxymethyl pyrimidine Racemic 2,4-diamino-5-(2,3-dichlorophenyl)-6-hydroxymethyl pyrimidine was prepared according to the procedure described in Reference Example 2. (+)-Di-p-toluoyl-D-tartaric acid (7.091 g) and the racemic (+/−)2,4-diamino-5-(2,3-dichlorophenyl)-6-hydroxymethyl pyrimidine (5 g) were heated to reflux in 60 ml of ethanol until all was in solution. The reaction mixture was then left to cool overnight at room temperature. The solid formed was then filtered off and dried in vacuo for 14 hours at 50° C.

The ratio of (−)2,4-diamino-5-(2,3-dichlorophenyl)-6-hydroxymethyl pyrimidine ("(−)enantiomer") to (+)2,4-diamino-5-(2,3-dichlorophenyl)-6-hydroxymethyl pyrimidine ("(+)enantiomer") in the dried material obtained (3.12 g, as determined by NMR analysis, was 82:18.

2.5 g of the above material was then dissolved in the minimum amount of ethanol (60 ml). The ethanol solution was left to cool overnight and filtered to give 1.74 g of chiral salt (70% recovery) after drying in vacuo at 50° C. for 14 hours. The ratio of (−)enantiomer to (+)enantiomer in the dried material was 95:5.

1.5 g of 95:5, (−):(+), material was recrystallised again from the minimum amount of ethanol (60 ml). The ethanol solution was left to stand overnight, then filtered and the resulting solid dried in vacuo at 50° C. for 5 and a half hours. The yield of crystalline material obtained (1.19 g) was 80%. The ratio of (−)enantiomer to (+)enantiomer was:

>98:2 by $^1$H NMR (DCl, methyl cyclodextrin as solvent)

99.8:0.2 by chiral HPLC on a Daicel Chirapak AD column (250×4.6 mm stainless steel), mobile phase 650:350 of hexane: propan-2-ol; ambient temperature; detection by UV at 254 nm; 20 μl of crystalline material dissolved in 20 ml of ethanol injected; flow rate 1.0 ml/min; attenuation 0.05 aufs.

2. Preparation of R(−)-2,4-Diamino-5-(2,3-dichlorophenyl)-6-fluoromethyl pyrimidine The (−)enantiomer (0.13 g, 0.00046 mole) produced in step 1 was cooled in dichloromethane (2×2 ml) to below −50° C. To the suspension was added diethylaminosulphur trifluoride (DAST) (0.153 g, 0.00115 mole). After 1 hour, the reaction mixture was warmed to −10° C. After 40 minutes, the resulting orange-coloured solution was cooled to below −50° C. prior to adding saturated sodium bicarbonate solution (1.6 ml). The whole was extracted with ethyl acetate and the combined extracts were washed with water, saturated brine and dried over $MgSO_4$. The filtrate was concentrated to give an off-white product on trituration with petroleum ether 60/80 (80 mg, 61% yield): 99.6% of the R-(−)-enantiomer, and 0.4% of the S-(+)-enantiomer.

EXAMPLE 4

Preparation of R(−)-2,4-diamino-5-(2,3-dichlorophenyl)-6-fluoromethyl Pyrimidine Isethionate AG1×8 ion exchange resin (50 mesh) was initially converted from the chloride form to the isethionate form by eluting with aqueous sodium isethionate. After washing with water, the column was eluted with dilute HCl to give isethionic acid as an aqueous solution which was then titrated against dilute sodium hydroxide solution.

0.46M isethionic acid (11.35 ml, 1.0 eq) was added to a suspension of R(−)-2,4-diamino-5-(2,3-dichlorophenyl)-6-fluoromethyl pyrimidine (1.5 gms, 5.22 mmol) in water (100 ml). The solution was then filtered and freeze-dried to give the product as a cream solid.

Yield 2.1 gms (89%). mg 85–90° C.

EXAMPLE 5

Preparation of R(−)-2,4-diamino-5-(2,3-dichlorophenyl)-6-fluoromethyl Pyrimidine Methanesulphonate Methanesulphonic acid (0.158 ml, 0.234 g, $2.39 \times 10^{-3}$ mole) was added to a suspension of R(−)-2,4-diamino-5-(2,3-dichlorophenyl)-6-fluoromethyl pyrimidine in dry ether (21 ml). The resulting mixture was stirred at room temperature for 2 hrs. The suspension was filtered, washed well with dry ether (5 ml), sucked dry and dried under vacuum at room temperature.

Yield 0.911 g (93%). M.p. 245–247° C.

EXAMPLE 6

Preparation of R(−)-2,4-diamino-5-(2,3-dichlorophenyl)-6-fluoromethyl Pyrimidine Monohydrochloride R(−)-2,4-Diamino-5-(2,3-dichlorophenyl)-6-fluoromethylpyrimidine (0.70 g, 0.0024 mole) was suspended in ethereal hydrochloric acid (5.60 ml) and stirred at room temperature for 2 hours. The suspension was filtered, washed well with dry ether (×2,10 ml), sucked dry and dried under vacuum at room temperature to give a white solid.

Yield 0.773 g. (98%). M.p. 232–235 C

Properties Of (−)-2,4-Diamino-5-(2,3-dichlorophenyl)-6-Hydroxymethyl Pyrimidine

| | | |
|---|---|---|
| Physical appearance: | white solid | |
| Melting point: | 179–181° C. | |
| Molecular formula: | $C_{11}H_{10}Cl_2N_4O$ | |
| Molecular weight: | 331.20 | |
| Optical rotation: | $[\alpha]_D^{26} =$ | −49.06° (c = 0.5, EtOH) |
| | $[\alpha]_{Hg546}^{26} =$ | −54.82° (c = 0.5, EtOH) |
| Optical rotation for (+)enantiomer: | $[\alpha]_{Hg546}^{23} =$ | +65.09° (c = 0.5, EtOH) |
| | $[\alpha]_D^{23} =$ | +32.05° (c = 0.5, EtOH) |

NMR data:

7.62 (doublet of doublets (dd), 1H, 4'); 7.39 (triplet (t), 1H, 5'); 7.23 (dd, 1H, 6'); 6.08 (singlet (s), 2H, 2-$NH_2$); 5.83 (s, 2H, 4-$NH_2$); 4.55 (t, 1H, OH); 3.85 (t, 2H, $CH_2$)

Properties of R(−)-2,4-Diamino-5-(2,3-dichlorophenyl)-6-fluoromethyl Pyrimidine

1. Chemical/Physico-chemical properties

| | |
|---|---|
| Physical appearance: | white solid |
| Melting point: | 215–216° C. |
| Molecular formula: | $C_{11}H_9Cl_2FN_4$ |
| Molecular weight: | 287.13 |
| Optical rotation: | $[\alpha]_D^{25.5}$ = −56.75° (c = 0.53, EtOH) |
| | $[\alpha]_{Hg546}^{25.5}$ = −72.07° (c = 0.53, EtOH) |
| Optical rotation for S(+)-enantiomer: | $[\alpha]_D^{25.5}$ = +59.20° (c = 0.52, EtOH) |
| | $[\alpha]_{Hg546}^{25.5}$ = +70.00° (c = 0.52, EtOH) |

NMR data:

7.65 (dd, 1H, 4'); 7.39 (t, 1H, 5'); 7.23 (dd, 1H, 6'); 6.15 (s, 2H, 2-$NH_2$); 5.98 (s, 2H, 4-$NH_2$); 4.88 (quartet (q), 1H, $CH_2F$); 4.64 (q, 1H, $CH_2F$)

2. Activity against dihydrofolate reductase (DHFR) activity

R(−)-2,4-Diamino-5-(2,3-dichlorophenyl)-6-fluoromethyl pyrimidine, its S(+)enantiomer and lamotrigine were assayed for activity against rat liver DHFR using a spectrophotometric assay. The assay was a modification of that set out in Biochemical Pharmacology 20, 561–574, 1971. The results are as follows:

R(−)enantiomer=25% inhibition at 100 $\mu$M

S(+)enantiomer=33% inhibition at 100 $\mu$M

Lamotrigine: $IC_{50}$=119.6 $\mu$M

3. Inhibition of glutamate release

The R(−)enantiomer, S(+)enantiomer and lamotrigine were tested for their effect on veratrine-evoked glutamate release from rat brain slices according to the protocol described in Epilepsia 27, 4.90497, 1986. The results obtained are as follows:

R(−)enantiomer: 64% inhibition at 10 $\mu$M

S(+)enantiomer: 0% inhibition at 10 $\mu$M

Lamotrigine: $IC_{50}$=21 $\mu$M

4. Activity against voltage-gated sodium channel:,

Recombinant rat type IIA channels

The action of the R(−)enantiomer on rat typos IIA sodium channels stably expressed in chinese hamster ovary cells was studied using whole-cell recording techniques, and compared with lamotrigine. Both the R(−)enantiomer (1–500 $\mu$M) and lamotrigine produced an inhibition of $Na^+$ currents in a concentration-dependent and voltage-dependent manner. The $IC_{50}$'s at two different holding potentials ($V_h$) were as follows:

| | |
|---|---|
| R(−)enantiomer: | 18 $\mu$M at $V_h$ = −60 mV |
| | 160 $\mu$M at $V_h$ = −90 mV |
| Lamotrigine: | 98 $\mu$M at $V_h$ = −60 mV |
| | 413 $\mu$M at $V_h$ = −90 mV |

Native channels (a) Cultured rat striatal neurones

The action of the R(−)enantiomer on native channels in cultured rat striatal neurones was studied using whole-cell recording techniques. The compound produced a concentration- and voltage-dependent inhibition of $Na^+$ currents. The $IC_{50}$ at a holding potential ($V_h$) of 60 mV was about 8 $\mu$M, compared with a much lower potency at $V_h$=−90 mV. The inhibition produced by 10–30 $\mu$M of the R(−)enantiomer was virtually eliminated by hyperpolarising the cells to $V_h$=−120 mV (b) Cultured embryonic rat hippocampal neurones The effects of the R(−)enantiomer, the S(+)enantiomer and lamotrigine on whole-cell sodium currents in cultured rat hippocampal neurones were studied using patch-clamp techniques. Sodium currents were elicited by the application of 20 msec dipolarisng pulses, thereby lowering membrane potential to −10 mV from a holding potential of −60 mV. All three compounds showed a concentration-dependent reduction of peak sodium current, with $IC_{50}$'s as follows:

R(−)enantiomer: 4 $\mu$M

S(+)enantiomer: 20 $\mu$M

Lamotrigine: 16 $\mu$M

5. Analgesic activity

Effects on the development of $PGE_2$-induced acute hyperalgesia

The R(−)enantiomer, S(+)enantiomer and lamotrigine were given orally to rats 1 h before subplantar injection of $PGE_2$ (100 ng). Reaction times to paw pressure were measured 3 h after $PGE_2$ injection. Ataxia was scored at the same time by observation of the rats placed in an arena. The results are shown in Table 1 below. Ataxia is presented as the ratio between the ataxia and analgesia $ED_{50}$s, p.o., n=5.

TABLE 1

| Compound: | Analgesia $ED_{50}$ (mg/kg) (95% limits) | Ataxia ratio |
|---|---|---|
| R(−)enantiomer | 2.5 (2.2–2.9) | 10.0 |
| S(+)enantiomer | 50.1 (39.2–70.5) | >2 |
| Lamotrigine | 34.8 (26.9–53.2) | 2.3 |

Effects on established $PGE_2$-induced acute hyperalgesia

The R(−)enantiomer was given orally 2 h after subplantar injection of $PGE_2$ (100 ng) when the hyperalgesia was established. Reaction time to paw pressure was measured 3 h after the $PGE_2$ administration. The analgesia $ED_{50}$ and 95% confidence limits were 3.4 (3.1–3.7) mg/kg.

6. Anticonvulsant activity

Maximal electroshock test

This seizure model uses ear-clip electrodes, and is sensitive to antiepileptic agents used clinically to control clonic/tonic (grand mal) and partial seizures with secondary generalisation (Swinyard, J. Am. Pharm. Ass. 38, 201–204, 1949; Loscher and Schmidt, Epilepsy Res. 2, 1.45–181, 1988).

(a) Duration of action

The R(−)enantiomer, S(+)enantiomer and lamotrigine were tested intraperitoneally (i.p.) in rats at various time intervals after injection. The $ED_{50}$ values shown below in Table 2 are doses preventing hind-limb extension in 50% of the animals.

TABLE 2

| Time interval (hours) | R(−)enantiomer $ED_{50}$ (95% limits) (mg/kg) | S(+)enantiomer $ED_{50}$ (95% limits) (mg/kg) | Lamotrigine $ED_{50}$ (95% limits) (mg/kg) |
|---|---|---|---|
| 0.5 | 1.3 (0.9–1.9) | 17.6 (11.6–26.4) | 2.7 (1.8–4.0) |
| 1 | 1.0 (0.7–1.5) | 19.0 (12.7–28.5) | 3.3 (2.3–4.0) |
| 2 | 1.2 (0.8–1.7) | 30.7 (20.9–45.3) | 2.7 (1.8–3.9) |
| 4 | 2.3 (1.6–3.4) | 87.3 (47.7–168) | 2.3 (1.5–3.3) |
| 8 | 5.9 (4.0–8.7) | N/T (not tested) | 4.8 (3.3–7.1) |
| 24 | 12.9 (9.0–19.1) | N/T | 7.1 (4.6–11.0) |

These data show that the R(−)enantiomer is a potent anticonvulsant, 2–3 times more active than lamotrigine and 15–20 times more active than its S(=)enantiomer. In addition, the isethionate addition salt of the R(−) enantiomer (calculated as the base) was equiactive with the R(−) enantiomer base by the i.p. route ($ED_{50}$s at 2 hrs: 1.8 and 2.5 mg/kg respectively; $p<0.05$).

In a separate series of experiments, the half-life ($t_{1/2}$) for the R(−)enantiomer in male rats was 5.4 hrs compared with a $t_{1/2}$ of 3.1 hrs for the S(+)enantiomer.

(b) Different routes of administration

The R(−)enantiomer and lamotrigine were evaluated in mice tested 1 hour after drug administration by various routes. The results are shown in Table 3 below.

TABLE 3

| Compound | Route | $ED_{50}$ mg/kg (95% limits) |
|---|---|---|
| R(−)enantiomer | i.p. | 1.3 (0.93–1.8) |
|  | p.o. | 1.2 (0.85–1.7) |
|  | s.c. | 0.96 (0.68–1.4) |
| Lamotrigine | i.p. | 2.3 (1.6–3.3) |
|  | p.o. | 3.3 (2.3–4.8) |
|  | s.c. | 1.8 (1.2–2.5) |

In a separate study, the R(−)enantiomer isethionate was evaluated by the i.v. route in rats tested 1 hour after drug administration. A stronger current (200 mA) was used compared with that (20 mA) used in the other procedures. The $ED_{50}$ for the R(−)enantiomer salt (calculated as the base) was 1.5 mg/kg ($ED_{50}$ for lamotrigine: 2.5 mg/kg).

These results demonstrate that the R(−)enantiomer is a potent anticonvulsant, approximately equiactive by the various routes tested and 2–3 times more potent than lamotrigine in the maximal electroshock test in rats and mice. The R(−)enantiomer has a long duration of action and is effective via all routes of administration.

7. Irritable Bowel Syndrome

Male Listar hooded rats weight range 100–150 g were used.

The rats were sensitised by dosing ip (1 ml per rat) with a solution containing egg albumin, (10 ug/ml) pertusssis vaccine (1 mg/ml) and aluminium hydroxide (10 mg/ml). Control animals received saline.

Seven days later the rats were anaesthetised using isofurane and the external oblique muscle exposed. Two nichrome wires were implanted into the muscles and the wires exteriorised to the back of the neck, the skin was sutured and the animals were allowed to recover.

Six days later the animals were fasted overnight. On the following day the animals were anaesthetised and the colorectum washed out using saline. A 4 cm long latex balloon tied to a portex cannula was connected to an inflation device, and the nichrome electrodes at the back of the neck were connected to head stage.

The electrical activity of the external oblique muscle was recorded by a data capture system ('spike2') which calculated the number of electrical spikes. Sequential pressure response curves (10–100 mmHg) in sensitised and the control animals were constructed. The balloon was inflated for 1 min at each pressure, followed by a rest period of 5 min.

The mean number of spikes at each pressure was calculated for the control animals, sensitised animals and sensitised animals treated with the R(−) enantiomer. The R(−) enantiomer or vehicle (0.25% methylcellulose) were administered orally (5 ml/kg), 60 minutes before starting the pressure response curve.

Results

In normal rats colorectal distension produced a pressure related increase in electrical activity in the abdominal muscles (pressures in excess of 40 mmHg approx). After sensitisation of the rats with egg albumin there was a marked increase in electrical activity of these muscles for a given distension (pressure), but also a decrease in the threshold for such activity (20 mmHg approx). The R(−) enantiomer at 10 mg/kg p.o. produced a complete reversal of the changes induced by egg albumin.

The results indicate that in conditions of hypersensitivity such as seen in irritable bowel syndrome, the R(−) enantiomer would be effective at reversing the hypersensitivity and therefore reduce the pain and dismotility associated with irritable bowel syndrome.

8. MPTP Induced Neurotoxic Model

Animals and Treatment

Six-week old male C57B1/6 mice (Japan SLC Co., Hamamatu) were housed ten per case in a temperature-controlled room under a 12-hours light/12-hours dark cycle with free access to food and water.

Mice received i.p. injections of the R(−) enantiomer and the S(+) enantiomer (30 mg/kg) in olive oil starting 12 hours before MPTP injection and every 12 hours for the next 5-injections. Control mice received olive oil only.

Mice receive s.c. injection of MPTP-HCl (40 mg of free base per kg; Research Biochemicals) in saline. Control mice received saline only.

Measurement of Striatal Dopamine Levels

HPLC with electrochemical detection was used to measure striatal levels of dopamine (J.C. Garcia': Journal of Chromatography B. 656 (1994) 77–80).

Seven days after the MPTP injection, mice (7.9 per group) were killed and striata were dissected out, immediately frozen, and stored at −80° C. until analysis. On the day of the assay, tissue samples were sonicated in 10 vol(wt/vol) of 0.1M perchloric acid /1.9 mM sodium hydrogen sulfite containing 1.6μg/ml 3,4-dihydroxybenzylamine hydrobromide(Sigma) as an internal standard. After centrifugation (2,800× g for 10 min at room temperature) and filtration (0.5 μm; Millipore membrane filter), 10 μl of supernatant was injected onto an Inertsil ODS3 column (4.6×250 mm; GL Science, Tokyo). The mobile phase consisted of 88% 115 mM $NaH_2PO_4$/0.178 mM $Na_2EDTA$ /0.92 mM 1-octanesulfonic acid (pH=2.6) solution and 12% ethanol. F low rate was 1.0 ml/min. Peaks were detected by a Shimazu electrochemical detector LECD-6A(700 mV).

TABLE 4

Dopamine contents in the striatum of MPTP injected C57B116 mice

| Treatment | n | Dopamine (μg/g wet tissue) | % protection | dead/used (% mortality)† |
|---|---|---|---|---|
| Saline (s.c.) + Olive oil (i.p.) | 8 | 13.84 ± 2.27 |  | 0/8 (0) |
| MPTP(1 × 40 mg/kg. s.c.) + Olive oil (i.p.) | 9 | 6.50 ± 3.38 |  | 0/9 (0) |

TABLE 4-continued

Dopamine contents in the striatum of MPTP injected C57B116 mice

| Treatment | n | Dopamine ($\mu$g/g wet tissue) | % protection | dead/used (% mortality)† |
|---|---|---|---|---|
| R(−) enantiomer (30 mg/kg, i.p.) | 7 | 12.45 ± 1.18 | 81.0 | 0/7 (0) |
| S(+) enantiomer (30 mg/kg, i.p.) | 7 | 7.99 ± 1.55 | 20.3 | 0/7 (0) |

Test-compounds were intraperitoneally administered 6 times (12 hour intervals) during day −1 to day 2. MPTP or saline was subcutaneously injectioned on day 0. Mice were sacrificed by cervical dislocation on day 7. Dopamine content in the striatum was measured using HPLC-ECD system.
† % mortality during day −1 to 7.

Solubility and Stability Studies on Salts of R(−)-2,4-Diamino-5-(2,3-dichlorophenyl)-6-fluoromethyl Pyrimidine 1. Experimental Salts 10 mg of each of the acetate, benzoate, HCl, tosylate, benzylate, succinate, salicylate, tartrate, (L)-lactate, sulphate, fumarate, citrate, malonate, phosphate, naphsylate and mesylate salts of R(−)-2,4-diamino-5-(2,3-dichlorophenyl)-6-fluoromethyl pyrimidine were synthesised.

Melting Profile

Events on heating were monitored visually using a Mettler hotstage and a microscope. A DSC scan was then used to confirm the observed events and identify the type of event. The DSC experiments were performed using the Perkin Elmer DSC-7 system with a TAC7/DX recorder. In order to capture as many events as possible a scan irate of 10° C./min and 1–2 mg sample size was used. DSC sweeps between 40° C. and 400° C. or from and to 50° C. outside any event observed on the hot stage were carried out on one or two samples. The samples and reference (air) were placed in 50 $\mu$l aluminium pans with holes.

Solubility and pH

The solubility was determined by means of the drug addition method. At room temperature the drug was added to 0.25 ml deionised water. The sample was diluted to 2 ml for pH determination. A single determination was carried out.

2. Results

Table 5 below indicates the melting profile of the salts, as determined using a Mettler hotstage and the DSC:

TABLE 5

| Salt | Hydrate | Hotstage results | | DSC result onset temp | | Hotstage/DSC results indicates | Possible good stability profile |
|---|---|---|---|---|---|---|---|
| Acetate | + | Partial melt | 171–200° C. | Dehydrate onset | 119° C. | Racemisation | |
| | | Recryst. | 181–215° C. | Melt | 184° C. | at temp similar | |
| | | Melt | 232–233° C. | Recryst. | 197° C. | to base | |
| | | | | Melt. | 218° C. | (200° C.) | |
| Benzoate | + | Partial melt | 48–58° C. | Melt onset | 160° C. | Sample | |
| | | Recryst. | 85–131° C. | Melt | 220° C. | unstable from | |
| | | Melt. | 131–160° C. | | | low temp. | |
| | | Recryst. | 171–200° C. | | | | |
| | | Melt | 234–237° C. | | | | |
| HCl | − | Partial melt | 220° C. | Recryst. | 243° C. | Racemisation | X |
| | | Sample went brown over 230° C. | | | | at higher temp then base 243° C. | |
| Toluene-sulphonate | + | Partial melt | 41° C. | Run did not pick up melt | | No-racemisation | X |
| | | Total melt | 98° C. | | | | |
| Benzene-sulphonate | + | Total melt | 98° C. | Run did not pick up melt | | No-racemisation | X |
| Succinate | + | Crystals | 88–120° C. | Recryst. | 81° C. | Racemisation | |
| | | Partial melt | 150–152° C. | Melt | 141° C. | 81° C. | |
| | | Sec. melt | 164–170° C. | Melt | 155° C. | | |
| | | Third melt | 222–228° C. | | | | |
| Salicylate | + | Bright cryst. | 72–82° C. | Melt | 60° C. | Racemisation | |
| | | Melt | 76° C. | Melt | 182° C. | 60° C. | |
| | | Melt | 170° C. | | | | |
| Tartrate | + | Melt | 178° C. | Dehydration | 134° C. | No-racemisation | X |
| | | | | Melt | 180° C. | | |
| (L)-Lactate | + | Melt | 50° C. | Broad melt from | 110° C. | Racemisation | |
| | | | | Recryst. | 143° C. | 143° C. | |
| Sulphate | + | Recryst. | 191–198° C. | Dehydrate | 175° C. | Racemisation | X |
| | | Melt | 221–224° C. | Melt | 194° C. | 194° C. | |
| | | | | Recryst. | 207° C. | equivalent to | |
| | | | | Melt | 215° C. | base | |
| Fumarate | + | Partial melt | 115–120° C. | Melt | 100° C. | Racemisation | |
| | | Partial melt | 186° C. | Recryst. | 127° C. | 127° C. | |
| | | Melt | 210° C. | Melt | 173° C. | | |
| | | | | Melt | 200° C. | | |

TABLE 5-continued

| Salt | Hydrate | Hotstage results | | DSC result onset temp | | Hotstage/DSC results indicates | Possible good stability profile |
|---|---|---|---|---|---|---|---|
| Citrate | + | Partial melt Melt | 117–119° C. Dehydrate 129–132° C. Melt | 104° C. 140–172° C. | | No-racemisation | X |
| Malonate | + | Melt | 72–79° C. Melt | 117° C. | | No-racemisation | X |
| Phosphate | + | Melt | 57–73° C. Melt | 67° C. | | No-racemisation | (X) |
| Naphthalene-disulphonate | + | No melt below | 300° C. Dehydration Melt | 352° C. 370° C. | | No-racemisation | X |
| Methane-sulphonate | – | Partial melt Recryst. Total melt | 239° C. Melt 240° C. 249° C. | 245° C. | | Racemisation 240° C. | X |

Salts for which racemisation could not be observed on heating and compounds where racemisation occurred at a higher temperature than the free base were selected as candidates with ia potentially good stability profile. The tests suggested that the tosylate, benzylate, tartrate, sulphate, citrate, malonate, phosphate, naphsylate and mesylate could provide good stability. The tosylate, benzylate, malonate and phosphate salt melted below 100° C. Thus, these may be difficult to handle and may, therefore, be less suitable for formulation purposes.

Table 6 below shows the solubility of the salts in water at room temperature, converted to equivalent base, and the pH of the solution.

TABLE 6

| Salt | MW | Solubility (mg/ml) | Solubility of equivalent base mg/ml | pH | pH >3 & solubility >25 mg/ml |
|---|---|---|---|---|---|
| Acetate | 326 | 0.32 | 0.28 | 5.54 | |
| Benzoate | 479 | <0.66 | <0.4 | 4.17 | |
| HCl | 327 | 24–35 | 21–31 | 3.61 | X |
| Toluene-sulphonate | 606 | 17–33 | 8–16 | 2.17 | |
| Benzene-sulphonate | 551 | 20–23 | 10–12 | 2.43 | |
| Succinate | 520 | 3–22 | 2–12 | 4.09 | |
| Salicylate | 499 | 3–4 | 2–3 | 3–2 | |
| Tartrate | 476 | 8–12 | 5–7 | 3.48 | |
| (L)-Lactate | 467 | 1.8 | 1.1 | 3.43 | |
| Sulphate | 394 | >31* | >23* | 1.92 | |
| Fumarate | 505 | 3–8 | 2–5 | 3.04 | |
| Citrate | 540 | 6–12 | 3–6 | 3.99 | |
| Malonate | 466 | 13–23 | 8–14 | 3.2 | |
| Phosphate | 481 | >32* | >19* | 2.34 | |
| Napthalenedi-sulphonate | 571 | <0.37 | <0.2 | 3.27 | |
| Methane-sulphonate | 383 | >41* | >31* | 3.33 | X |
| Isethionate | 474 | 41.8 | 25.3 | 1.67 | |

*Sample not saturated

Table 6 shows that the solubility of four salts (acetate, benzoate, (L)-lactate, and naphsylate) were less than 1 mg/ml. These are, therefore, unlikely to be suitable for oral and IV use. Five salts (HCl, sulphate, phosphate, mesylate and isethionate) had a solubility of the equivalent base over or around 25 mg/ml, but only two of these also had a pH in solution over 3. A solution for injection should have a pH above 3 if adverse effects around the site of injection are to be avoided. From this test the HCL salt arid the mesylate salt are recommended for an intravenously injectable formulation.

PHARMACEUTICAL FORMULATION EXAMPLES

1. Tablets

Tablet 1

| | |
|---|---|
| R(-)enantiomer | 150 mg ) |
| Lactose | 200 mg ) |
| Maize Starch | 50 mg ) |
| Polyvinylpyrrolidone | 4 mg ) |
| Magnesium Stearate | 4 mg ) |

) = contents per tablet.

The R(-)enantiomer is mixed with the lactose and starch and granulated with a solution of the polyvinylpyrrolidone in water. The resultant granules are dried, mixed with the magnesium stearate and compressed to give tablets.

Tablet 2

The following ingredients were employed to prepare further tablets containing the R(-) enantiomer present in an amount of 5.0 mg, 25.0 mg, 35.0 mg, 50.0 mg, 75.0 mg and 150.0 mg in the respective tablet formulations.

TABLE 7

| | Quantity per Tablet (mg) | | | | | |
|---|---|---|---|---|---|---|
| R(-) enantiomer | 5.0 | 25.0 | 35.0 | 50.0 | 75.0 | 150.0 |
| Lactose | 200.2 | 180.2 | 170.2 | 155.2 | 130.2 | 55.2 |
| Hydroxypropyl Cellulose | 27.0 | 27.0 | 27.0 | 27.0 | 27.0 | 27.0 |
| Microcrystalline Cellulose | 27.0 | 27.0 | 27.0 | 27.0 | 27.0 | 27.0 |
| Povidone | 8.1 | 8.1 | 8.1 | 8.1 | 8.1 | 8.1 |
| Magnesium Stearate | 2.7 | 2.7 | 2.7 | 2.7 | 2.7 | 2.7 |
| Purified Water | 95 | 95 | 95 | 95 | 95 | 95 |
| Compression Weight | 270.0 | 270.0 | 270.0 | 270.0 | 270.0 | 270.0 |

The R(-) enantiomer, lactose, hydroxypropyl cellulose and microcrystalline cellulose were mixed together to form a dry powder mix. The Povidone was dissolved in purified water. The Povidone solution was added to the dry powder mix containing the R(-) enantiomer to obtain a moist mass with a 15 consistency suitable for granulation. The resulting moist mass was passed through a sieve, the granules dried and sifted. The magnesium stearate was added, followed by blending and compression.

2. Injections

Injection I

The methanesulphonate salt of the R(-)enantiomer is dissolved in sterile water for injection.

| Intravenous injection formulation II | |
|---|---|
| Methanesulphonate salt of the R(−)enantiomer | 200 g |
| Sterile, pyrogen-free phosphate buffer (pH 9.0) to | 10 ml |

The methanesulphonate salt is dissolved in most of the phosphate buffer at 35–40° C., then made up to volume and filtered through a sterile micropore filter into sterile 10 ml glass vials (Type 1) which are then sealed with sterile closures and overseals (calculated as the base).

In the following examples, the active ingredient: may be the R(−)enantiomer or a pharmaceutically acceptable acid addition salt thereof (calculated as the base).

3. Capsule formulations

Capsule Formulation I

Formulation I may be prepared by admixing the ingredients and filling two-part hard gelatin capsules with the resulting mixture.

| | mg/capsule |
|---|---|
| (a) Active ingredient | 250 |
| (b) Lactose B.P. | 143 |
| (c) Sodium Starch Glycollate | 25 |
| (d) Magnesium Stearate | 2 |
| | 420 |

| Capsule Formulation II | |
|---|---|
| | mg/capsule |
| (a) Active ingredient | 250 |
| (b) Macrogel 4000 BP | 350 |
| | 600 |

Capsules may be prepared by melting the Macrogel 4000 BP, dispersing the active ingredient in the melt, and filling two-part hard gelatin capsules therewith.

| Capsule Formulation III (Controlled-release capsule) | |
|---|---|
| | mg/capsule |
| (a) Active ingredient | 250 |
| (b) Microcrystalline Cellulose | 125 |
| (c) Lactose BP | 125 |
| (d) Ethyl Cellulose | 13 |
| | 513 |

The controlled-release capsule formulation may be prepared by extruding mixed ingredients (a) to (c) using an extruder, then spheronising and drying the extrudate. The dried pellets are coated with ethyl cellulose (d) as a controlled-release membrane and filled into two-part hard gelatin capsules.

| 4. Syrup formulation | |
|---|---|
| Active ingredient | 0.2500 g |
| Sorbitol Solution | 1.5000 g |

-continued

| 4. Syrup formulation | |
|---|---|
| Glycerol | 1.0000 g |
| Sodium Benzoate | 0.0050 g |
| Flavour | 0.0125 ml |
| Purified Water q.s. to | 5.0 ml |

The sodium benzoate is dissolved in a portion if the purified water and the sorbitol solution added. The active ingredient is added and dissolved. The resulting solution is mixed with the glycerol and flavour and then made up to the required volume with the purified water.

| 5. Suppository formulation | |
|---|---|
| | mg/suppository |
| Active ingredient (63 μm)* | 250 |
| Hard Fat, BP (Witepsol H15 - Dynamit Nobel) | 1770 |
| | 2020 |

*The active ingredient is used as a powder wherein at least 90% of the particles are of 63 μm diameter or less.

One fifth of the Witepsol H15 is melted in a steam-jacketed pan at 45° C. maximum. The active ingredient is sifted through a 200 μm sieve and added to the molten base with mixing, using a Silverson fitted with a cutting head, until a smooth dispersion is achieved. Maintaining the mixture at 45° C., the remaining Witepsol H15 is added to the suspension which is stirred to ensure a homogenous mix. The entire suspension is then passed through a 250 μm stainless steel screen and, with continuous stirring, allowed to cool to 40° C. At a temperature of 38–40° C., 2.02 g aliquots of the mixture are filled into suitable plastics moulds and the suppositories allowed to cool to room temperature.

We claim:

1. A pyrimidine of formula (I):

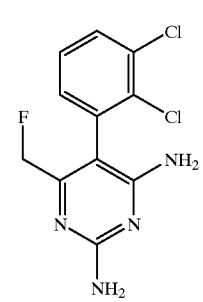

(I)

or an acid addition salt thereof.

2. A salt according to claim 1, which is a pharmaceutically acceptable acid addition salt.

3. A salt according to claim 1 which is the sulphate, phosphate or isothionate.

4. A salt according to claim 1 which is the hydrochloride or methanesulphonate salt.

5. A process for the preparation of a pyrimidine of claim 1 or an acid addition salt thereof, which process comprises:

(I) resolving racemic 2,4-diamino-5-(2,3-dichlorophenyl)-6-fluoromethyl pyrimidine with a suitable chiral acid and recrystallising the resulting salt so as to obtain a salt which consists substantially only of the salt with R(−)-2,4-diamino-5-(2,3-dichlorophenyl)-6-fluoromethyl pyrimidine; and (ii) if desired, converting the recrystallised salt to the free base or another acid addition salt as appropriate.

6. A process for the preparation of a pyrimidine of claim 1 or an acid addition salt thereof, which process comprises:

(a) resolving racemic 2,4-diamino-5-(2,3-dichlorophenyl)-6-hydroxymethyl pyrimidine with a suitable chiral acid and recrystallising the resulting salt so as to obtain a salt which consists substantially only of the salt with (−)-2,4-diamino-5-(2,3-dichlorophenyl)-6-hydroxymethyl pyrimidine;

(b) if desired, converting the recrystallised salt to the free base or another salt;

(c) fluorinating the recrystallised salt from step (a) or the free base or said other salt from step (b) under conditions at which racemisation of the (−)-2,4-diamino-5-(2,3-dichlorophenyl)-6-hydroxymethyl pyrimidine or the resulting (−)-2,4-diamino-5-(2,3-dichlorophenyl)-6-fluoromethyl pyrimidine does not occur; and (d) if desired, converting the resulting fluorinated compound into the free base or into an acid addition salt thereof as appropriate.

7. A pharmaceutical formulation comprising, as active ingredient, a pyrimidine of claim 1 or a pharmaceutically acceptable acid addition salt thereof and a pharmaceutically acceptable carrier or diluent.

8. A pyrimidine of formula (III):

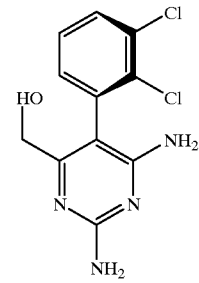

(III)

9. A method of treatment of functional bowel disorders, bipolar disorder, neurodegenerative disorders, or preventing or reducing dependence on, or preventing or reducing tolerance to, a dependence-inducing agent, said process comprising administering to a subject in need of same an effective amount of the pyrimidine of claim 1 or a pharmaceutically acceptable addition salt thereof.

* * * * *

UNITED STATES PATENT AND TRADEMARK OFFICE
CERTIFICATE OF CORRECTION

PATENT NO.        : 6,124,308
APPLICATION NO.  : 09/029162
DATED             : September 26, 2000
INVENTOR(S)       : Nobbs et al.

It is certified that error appears in the above-identified patent and that said Letters Patent is hereby corrected as shown below:

Column 1, lines 25-33
Should read:

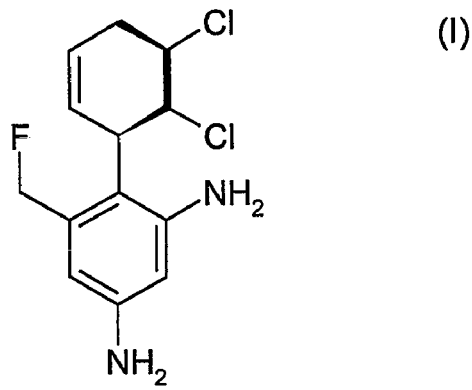

Claim 1, column 24, lines 42-55,
Should read:

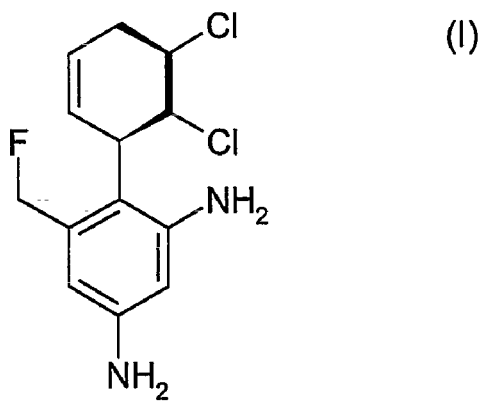

UNITED STATES PATENT AND TRADEMARK OFFICE
CERTIFICATE OF CORRECTION

PATENT NO. : 6,124,308
APPLICATION NO. : 09/029162
DATED : September 26, 2000
INVENTOR(S) : Nobbs et al.

It is certified that error appears in the above-identified patent and that said Letters Patent is hereby corrected as shown below:

Claim 9, column 26, line 19,
Should read:

--9. A method of treatment of pain, convulsions, functional bowel disorders, bipolar disorder, neurodegenerative disorders, or preventing or reducing dependence on, or preventing or reducing tolerance to, a dependence-inducing agent, said process comprising adminstering to a subjuct in need of same an effective amount of the pyrimidine of claim 1 or a pharmaceutically acceptable addition salt thereof.

10. R(-)-2,4,-diamino-5-(2,3-dichlorophenyl)-6-fluoromehtyl pyrimidine or an addition salt thereof.--

Signed and Sealed this

Twenty-fourth Day of October, 2006

JON W. DUDAS
*Director of the United States Patent and Trademark Office*

UNITED STATES PATENT AND TRADEMARK OFFICE
CERTIFICATE OF CORRECTION

PATENT NO.       : 6,124,308
APPLICATION NO.  : 09/029162
DATED            : September 26, 2000
INVENTOR(S)      : Nobbs et al.

Page 1 of 2

It is certified that error appears in the above-identified patent and that said Letters Patent is hereby corrected as shown below:

Column 1, lines 20-33
Should read:

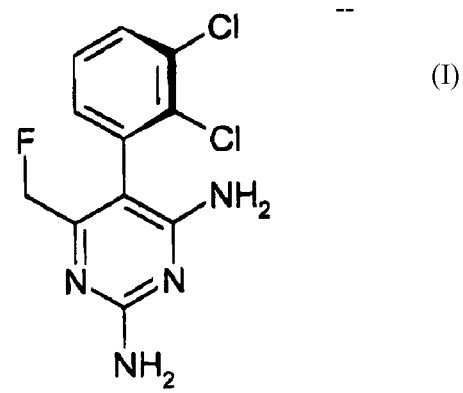

Column 24, lines 42-55,
Should read:

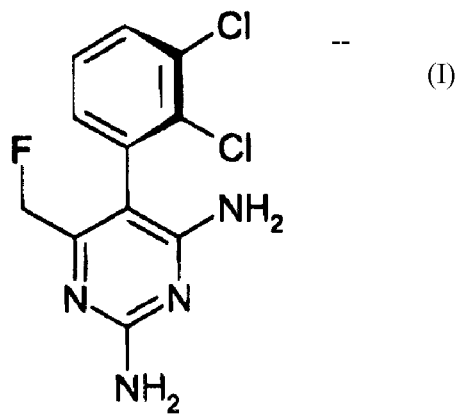

UNITED STATES PATENT AND TRADEMARK OFFICE
CERTIFICATE OF CORRECTION

PATENT NO. : 6,124,308
APPLICATION NO. : 09/029162
DATED : September 26, 2000
INVENTOR(S) : Nobbs et al.

It is certified that error appears in the above-identified patent and that said Letters Patent is hereby corrected as shown below:

Column 26, lines 19-30
Should read:

--9. A method of treatment of pain, convulsions, functional bowel disorders, bipolar disorder, neurodegenerative disorders, or preventing or reducing dependence on, or preventing or reducing tolerance to, a dependence-inducing agent, said process comprising administering to a subject in need of same an effective amount of the pyrimidine of claim 1 or a pharmaceutically acceptable addition salt thereof.

10. R(-)-2,4,-diamino-5-(2,3-dichlorophenyl)-6-fluoromethyl pyrimidine or an addition salt thereof.--

Signed and Sealed this

Eighth Day of April, 2008

JON W. DUDAS
*Director of the United States Patent and Trademark Office*